US008507433B1

(12) United States Patent
Schally et al.

(10) Patent No.: US 8,507,433 B1
(45) Date of Patent: Aug. 13, 2013

(54) CARDIOPROTECTIVE EFFECTS OF GHRH AGONISTS

(75) Inventors: Andrew V. Schally, Miami Beach, FL (US); Norman L Block, Hollywood, FL (US); Joshua Hare, Miami Beach, FL (US); Rosemeire Miyuki Kanashiro Takeuchi, Miami, FL (US)

(73) Assignees: University of Miami, Miami, FL (US); The United States of America, represented by the Deptartment of Veterans Affairs, Washington, DC (US)

( * ) Notice: Subject to any disclaimer, the term of this patent is extended or adjusted under 35 U.S.C. 154(b) by 0 days.

(21) Appl. No.: 12/914,023

(22) Filed: Oct. 28, 2010

(51) Int. Cl.
*A61K 38/25* (2006.01)
*C07K 14/60* (2006.01)
*A61P 9/10* (2006.01)

(52) U.S. Cl.
USPC ........ 514/11.2; 514/15.1; 514/21.3; 530/324; 930/120

(58) Field of Classification Search
None
See application file for complete search history.

(56) References Cited

PUBLICATIONS

Kanashiro-Takeuchi et al, 2010. PNAS. 107(6): 1604-2609.*
Izdebski et al (1995. Proc Natl Acad Sci U.S.A. 92(11):4872-6).*
Ehlers, 2001. Endocrine. 14(1): 137-141.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Phillips, J Pharm Pharmacology 53: 1169-1174, 2001.*
Granata et al (2009. Cardiovascular Research. 83: 303-312, published on-line Mar. 17, 2009).*
Cittadini et al (1997. J Am Coll Cardiol. 29: 1109-16).*
Aimaretti, et al. "GHRH and GH Secretagogues: Clinical Perspectives and Safety", Pediatr Endocrine/ Rev 2, (Nov. 2004) 2(1):86-92.
Bollano, et al. "Growth hormone alone or combined with metoprolol preserves cardiac function after myocardial infarction in rats", Eur J Heart Fail, (2001) 3:651-660.
Cittadini, et al. "Growth Hormone Attenuates Early Left Ventricular Remodeling and Improves Cardiac Function in Rats With Large Myocardial Infarction", *J Am Coll/Cardio*, (Apr. 1997) 29(5):1109-1116.
Corpas et al., "Growth Hormone (GH)-Releasing Hormone-(1-29) Twice Daily Reverses the Decreased GH and Insulin-Like Growth Factor-I Levels in Old Men", *J. Clin. Endoc. Metabol.*, (Aug. 1992) 75(2):530-535.

Frascarelli et al., "Effect of ghrelin and synthetic growth hormone secretagogues in normal and ischemic rat heart", *Basic Res Cardiol*, (Aug. 21, 2003) 98:401-405.
Granata, et al. "Growth hormone-releasing hormone promotes survival of cardiac myocytes in vitro and protects against ischaemia-reperfusion injury in rat heart", *Cardiovasc Res*, (Mar. 17, 2009) 83:303-312.
Izdebski, et al. "Synthesis and biological evaluation of superactive agonists of growth hormone-releasing hormone", *Proc Natl Acad Sci USA*, (May 1995) 92(11):4872-4876.
Kanashiro-Takeuchi, et al., "Activation of growth hormone releasing hormone (GHRH) receptor stimulates cardiac reverse remodeling after myocardial infarction (MI)", Proc Natl Acad Sci USA, (Dec. 27, 2011), 109(2):559-563.
Kanashiro-Takeuchi, et al., "Growth Hormone Releasing Hormone (GHRH) Receptor Dependency for Cardioprotective Repair", *American Heart Association Scientific Sessions*, Orlando, Florida, Nov. 12-16, 2011 (Abstract).
Kanashiro-Takeuchi, et al., "Growth Hormone Releasing Hormone (GHRH) Agonist Improves Cardiac Performance in the Chronic Model of Myocardial Infarction (MI) in Rats", *Best of AHA Specialty Conferences Poster Session: BCVS 2010*, Chicago, Illinois, Nov. 15, 2010 (Abstract).
Kanashiro-Takeuchi, et al., "Growth Hormone Releasing Hormone (Ghrh) Agonist Improves Cardiac Performance in the Chronic Model of Myocardial Infarction (MI) in Rats", *The Heart Failure Society of America (HFSA) 14th Annual Scientific Meeting*, San Diego, California, Sep. 12-15, 2010 (Abstract).
Kanashiro-Takeuchi, et al. "Cardioprotective effects of growth hormone-releasing hormone agonist after myocardial infarction", *Proc Natl Acad Sci USA*, (Jan. 21, 2010) 107(6):2604-2609.

(Continued)

*Primary Examiner* — Zachary Howard
(74) *Attorney, Agent, or Firm* — Pepper Hamilton LLP

(57) ABSTRACT

Whether the growth hormone (GH)/Insulin-like growth factor 1(IGF-I) axis exerts cardioprotective effects remains controversial; and the underlying mechanism(s) for such actions are unclear. Here we tested the hypothesis that growth-hormone releasing hormone (GHRH) directly activates cellular reparative mechanisms within the injured heart, in a GH/IGF-I independent fashion. Following experimental myocardial infarction (MI), rats were randomly assigned to receive, during a 4 week period, either placebo (n=14), rat recombinant GH (rrGH, n=8) or JI-38 (n=8; 50 µg/Kg/day), a potent GHRH-agonist. JI-38 did not elevate serum levels of GH or IGF-I, but markedly attenuated the degree of cardiac functional decline and remodeling after injury. In contrast, GH administration markedly elevated body weight, heart weight, circulating GH and IGF-I, but did not offset the decline in cardiac structure and function. Whereas, both JI-38 and GH augmented levels of cardiac precursor cell proliferation, only JI-38 increased anti-apoptotic gene expression. The receptor for GHRH was detectable on myocytes supporting direct activation of cardiac signal transduction. Collectively, these findings demonstrate that within the heart GHRH-agonists can activate cardiac repair following MI, suggesting the existence of a potential signaling pathway based on GHRH in the heart. The phenotypic profile of the response to a potent GHRH agonist has therapeutic implications.

2 Claims, 11 Drawing Sheets

(56) References Cited

PUBLICATIONS

Takeuchi, et al. "Growth-Hormone-Releasing-Hormone (GHRH) Agonist as a Potential Cardioprotective Agent in Rats with Post-Myocardial Infarction (MI)", *American Heart Association*, Jun. 8, 2009 (Abstract).

Kiaris, et al., "Ligand-dependent and -independent effects of splice variant 1 of growth hormone-releasing hormone receptor", *Proc Natl Acad Sci USA*, (Aug. 5, 2003), 100(16):9512-9517.

Kiaris et al., "Extrapituitary effects of the Growth Hormone-Releasing Hormone", *Vitam Horm*, (2005) 70:1-24.

Marleau et al., "Cardiac and peripheral actions of growth hormone and its releasing peptides: Relevance for the treatment of cardiomyopathies", *Cardiovasc Res*, (2006) 69:26-35.

Mill, et al. "The Early Administration of Growth Hormone Results in Deleterious Effects on Ventricular Remodeling After Acute Myocardial Infarction", Arq Bras Cardiol, (Feb. 2005) 84(2):115-121.

Omerovic, et al. "Growth Hormone Improves Bioenergetics and Decreases Catecholamines in Postinfarct Rat Hearts", Endocrinology, (2000) 141(12):4592-4599.

Schally, et al., *Growth Hormone Secretagogues in Clinical Practice*, (Ch. 10), (1998), pp. 131-142, Marcel Dekker, Inc., New York.

Shen, et al. "GH replacement fails to improve ventricular function in hypophysectomized rats with myocardial infarction", Am J Physiol, (Nov. 1996) 271(5 Pt 2):H1721-H1727.

Tivesten, et al. "The Growth Hormone Secretagogue Hexarelin Improves Cardiac Function in Rats After Experimental Myocardial Infarction", Endocrinology, (2000) 141(1):60-66.

\* cited by examiner

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
acctccgact ttctcagttc ctgtatgccc                                      30

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
atcctgcgtc tggacctggc tggc                                            24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctgctttct ctaggtccct gt                                              22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggtttccct gggccttgg                                                  19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggttacgcg ctccctcat                                                  19

<210> SEQ ID NO 6
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 6
gtcacgcacg atttccctct c                                              21
```

CARDIOPROTECTIVE EFFECTS OF GHRH AGONISTS

RELATED APPLICATIONS

This application claims priority of copending application U.S. Ser. No. 61/289,949 filed Dec. 23$^{rd}$ 2009. This work was supported by NIH grant R01-AG025017, RO1-HL084275, RO1-HL65455, RO1-HL094848 and by National Heart, Lung, and Blood Institute Grants U54-HL081028. The studies in the laboratory of AVS were supported in part by The Medical Research Service of the Veterans Affairs Department and South Florida Veterans Affairs Foundation for Research and Education and University of Miami, Miller School of Medicine, Departments of Pathology and Medicine, Division of Hematology/Oncology (all to AVS and NLB).

FIELD OF THE INVENTION

Cardioprotective effects of GHRH Agonists

DISCUSSION OF THE PRIOR ART

Congestive heart failure remains a leading cause of morbidity and mortality in developed countries. Despite major therapeutic advances, current therapies fail to fully reverse heart failure and/or left ventricular (LV) dysfunction. One major therapeutic avenue is that of cytokine and/or hormonal signaling pathways, and in this regard, various experimental and clinical studies have suggested an important role for the GH/IGF-I axis in the regulation of cardiac growth regeneration and function (41, 42). Moreover, several clinical studies have tested the impact of GH replacement on the failing human heart, with controversial results (3, 4).

In addition to GH itself and IGF-I, GH releasing peptides such as ghrelin and synthetic GH secretagogues are also suggested to have cardiac effects (45-48) and GHRH mRNA is detected in peripheral tissues, including the heart (40, 10) consistent with widespread biological signaling potential beyond the hypothalamic-pituitary axis.

Recently, Granata et al. (10) reported that rat GHRH (1-44) promoted survival of cardiomyocytes in vitro and protected rat hearts from ischemia-reperfusion injury. The detection of the GHRH receptor on the cardiomyocyte sarcolemmal membrane supports the view that GHRH may elicit direct signal transduction within the heart, independent of the GH/IGF-I axis, per se (10). Ghrelin and other GH secretagogues may have pharmacological potential (10), but also have pleiotropic actions with a high possibility of unexpected side effects and potentially serious disadvantages. Thus, the administration of GHRH offers a potentially highly physiological approach based on direct action without known side effects or the necessity to activate the GH/IGF-I axis (11, 12). Furthermore, synthetic GHRH agonists, such as JI-38 (GHRH-A) are more potent and longer acting agents than native GHRH (13). Here we tested the hypothesis that GHRH-A has a favorable cardiac effect, attenuating the progressive decrease of cardiac function associated with post-Myocardial infarction left ventricular (MI LV) remodeling. In addition, we investigated the conjecture that GHRH directly activates signaling within the heart (10) and exerts effects on cellular reparative pathways.

SUMMARY

There is provided method of treating cardiac disease by activating the growth hormone releasing hormone pathway, particularly where the cardiac disease is selected from the group consisting myocardial infarction, myocardial ischemia, myocardial fibrosis, cardiac weakness, cardiac failure and cardiac inefficiency, especially where heart disease is congestive heart failure.

The method comprises administering to the patient in need of same a growth hormone releasing hormone receptor activating agent such as a peptide in particular a synthetic peptide.

The main finding of the present study is that GHRH-A has a cardioprotective role in vivo following acute MI. Animals receiving GHRH-A had improved cardiac structure and function and reduced infarct size. In addition, cardiac fibrosis, which is one of the main biological determinants of poor prognosis in heart failure, and strongly associated with severe arrhythmias, diastolic dysfunction and sudden death (14), was markedly reduced in the GHRH-A group but not in the rrGH group. The cardiac effects of GHRH-agonist appear to be direct, not involving the GH/IGF-I axis, since the circulating levels of these hormones were not increased by GHRH-A treatment.

The current findings can be viewed in the context of previous evaluations of the GH/IGF-I axis that have yielded variable results. The inconsistent and contradictory effects of GH or IGF-I administration on experimental post-MI models have been shown to be dependent on the timing of the treatment, the stage of the disease at treatment initiation, different dosing regimens (8) and might be related to the heterogeneous origin of treatment (15). In most of the studies early treatment with recombinant human GH have shown improvement in cardiac function and reduction on the LV remodeling (45, 16, 17) while other studies did not show beneficial effects (15, 18). Similarly, treatments with rat recombinant GH did not show beneficial effect in rats with large MI (19). Conversely, in rats all studies starting late after MI showed improvement on cardiac function (20-22). Importantly, all treatments with recombinant human GH in rats had a clear limitation due perhaps to the production of anti-GH antibodies after 2 weeks of treatment (23). Therefore, the long-term effects (either beneficial or deleterious) remain unknown in these models (48).

Our findings demonstrate that rrGH markedly increases body weight (BW), heart weight (HW) and circulating levels of GH and IGF-I, but does not improve cardiac function or prevent remodeling; on the contrary, rats treated with rrGH exhibited larger chambers and worse ejection fraction (EF). These results are in agreement with a study which showed that GH caused adverse effects on the process of LV remodeling (18).

An alternative approach for increasing systemic levels of GH is the administration of GH secretogues (GHS) such as Ghrelin (24) or a synthetic GHS peptides such as hexarelin (20, 25). Nagaya et al. (24) showed that ghrelin improved LV function and attenuated cardiac remodeling in a chronic heart failure model; however, these results were attributed to both GH/IGF-I dependent and GH-independent vasodilatory effects of ghrelin. Similarly, Tivesten et al (6) showed that hexarelin increased stroke volume and reduced total peripheral resistance. In contrast, Shen et al (19) reported increased survival rate, but no hemodynamic beneficial effect of GH-releasing peptide in dogs subjected to transient coronary occlusion, suggesting that these effects were mediated by GHS receptors rather than through the GH/IGF-I axis (that is by a GH independent pathway). To date, only one study in vitro has shown cardioprotective and a direct effect of GHRH (10). In that study, GHRH cardioprotection was demonstrated in isolated rat hearts subjected to ischemia-reperfusion injury, while in our work, cardiac function was assessed by echocardiography and in vivo closed-chest LV catheterization in rats subjected to a permanent occlusion. The mechanism underlying the differences between GHRH and GH effects is unclear. Post-receptor signaling cascades can be one reason for differences in activity between GHRH and GH. GHRH actions involve the stimulation of its receptor (GHRHR), a G protein-coupled receptor that activates at least two transduction pathways, the adenyl cyclase (AC)/cAMP/protein kinase A (PKA) via the $G_s$ subunit (26), and the Ras/MAPK pathway through the subunits (27).

The activation of the ERK1/2 signaling pathway has been connected with several cellular activities such as proliferation, differentiation, and survival, and ghrelin has previously been shown to activate both ERK1/2 and the serine threonine kinase Akt (28). GHRH induces activation of cAMP and a significant activation of the Akt and ERK1/2 survival pathways as has been demonstrated by Western blotting after GHRH administration. The PI3k/Akt pathway is a well known signaling pathway for cell protection, and recently, Granata et al (10) reported that ERK1/2 and PI3k/Akt are involved in survival effects induced by GHRH and found that GHRH increased ERK1/2 and Akt phosphorylation, cAMP, and phosphorylation on serine 133 of CREB. Recently, Lorenz et al (29) proposed that specific phosphorylation events on ERK 1/2 integrate differing upstream signals to induce hypertrophy. Hexarelin has also previously been shown to promote neuroprotection through activation of the P13/Akt pathway (30). Moreover, the PI3k/Akt pathway controls cell size, including cardiomyocyte size (31) and is associated with cardiomyocyte hypertrophy and apoptosis (30, 32).

Traditionally, the adult heart has been considered a postmitotic organ where the cardiac myocytes were terminally differentiated without ability to divide. However, several investigators (33-35) have suggested that at least a subpopulation of myocytes re-enter the cell cycle and divide, and also that a pool of cardiac stem cells may reside in the myocardium. In the present study, the expression of $Ki_{67}$ positive cells was significantly higher at the remote zone but only in the rrGH group and this was accompanied by an increase in capillary density in the same group. Previous study has documented that GH is able to stimulate mature cardiac myocytes to re-enter the cell cycle, divide and thereby increase their number in rat myocardium (36). A reduction in apoptosis would also lead to an increased number of cardiac myocytes but in our study, surprisingly, the reduction in apoptosis in both treated groups was lower and not statistically significant when assessed by TUNEL assay; however, at the molecular level, changes in the expression of Bax and Bcl2 supported an anti-apoptotic effect of GHRH-A.

We also examined the abundance of cardiac precursor cells which showed increased c-kit positive cells expression (clusters) in the infarct zone in both treated groups; recruitment of c-kit positive stem cells is associated with improvement in cardiac performance (37). Bruel et al (36) also reported that the number of c-kit positive cells in a GH treated group was 31% higher than that of the control group, but it was not statistically significant. Given the observation of similar increases in c-kit cells with GH and GHRH, yet greater reverse remodeling with GHRH, it is attractive to speculate that GHRH may stimulate cardiopoiesis to a greater extent. An alternate explanation is that the c-kit cells may traffic and/or proliferate to a greater or earlier extent. Finally, the findings of an anti-apoptotic milieu might suggest improved survival of differentiation cardiac precursor cells (CPCs). Future work is required to evaluate the direct effects of GHRH on CPC). Besides CPCs possess the IGF-I/IGF-I receptor system (38) which potentiates their survival and growth (39). Further studies are needed to ascertain whether GHRH-A or rrGH stimulated existing cardiac stem cells to differentiate into mature cardiac myocytes.

In summary, the present findings document that GHRH activation in the heart leads to reverse remodeling and recovery of functional performance to a greater degree than that due to GH, and that this occurs without stimulation of body weight or heart weight. These findings support ongoing basic and translational research into GHRH signal transduction mechanisms within the heart.

DESCRIPTION OF THE PREFERRED EMBODIMENTS

Material and Methods

Animal Model

MI induced by coronary artery ligation was performed in female 6-month-old Fisher-344 rats as described previously (40). Animals were randomly assigned to receive placebo, GHRH-agonist (GHRH-A [JI-38], 50 µg/kg) or rat recombinant GH (rrGH, 0.5 mg/kg) starting 2 hours post-surgery. All treatment was given subcutaneously twice daily for 4 weeks. The Institutional Animal Care and Use committee of University of Miami approved all protocols and experimental procedures.

Drugs

Rat recombinant GH (rrGH) was supplied by Dr. A. F. Parlow from National Hormone and Pituitary Program (NHPP) (UCLA-Harbor, Torrance, Calif.) and GHRH-A (JI-38) ([Dat$^1$, Gln$^8$, Orn$^{12,21}$, Abu$^{15}$, Nle$^{27}$, Asp$^{28}$, Agm$^{29}$]hGH-RH(1-29)NH$_2$, the non-coded amino acids are abbreviated as follows: Dat: desaminotyrosine, Orn: ornithine, Abu: aminobutyric acid, Nle: norleucine, Agm: agmatine) was made in the laboratory of one of us (AVS) (12, 13).

Results

As depicted in Fig. S1A, baseline body weight (BW) was similar in all groups. In the placebo group, MI significantly reduced BW from 225±4 to 208±3 g (p<0.05), an effect that was fully prevented by administration of GHRH-A (from 231±5 to 225±3 g). Conversely, rrGH increased BW from 217±4 to 256±3 g (p<0.01). Heart weight (HW) was increased in concert by rrGH (850±38 mg) in comparison to placebo (674±14 mg) or GHRH-A (695±26 mg) (p<0.0001 for both, Fig. S1B). Accordingly, the HW/BW ratios (Fig. S1C) were similar in all groups.

Growth Hormone and Insulin-Like Growth Factor-I Levels

To test the impact of rrGH and GHRH-A on the GH-IGF-I axis we measured circulating levels of these hormones (Fig. S2A-B). Whereas treatment with GHRH-A did not increase serum levels of either GH or IGF-I relative to placebo, treatment with rrGH led to marked increases in GH (679±196 vs. 64±23 ng/ml, P<0.01) and IGF-I (1052±91 vs. 553±46 ng/ml, p<0.01) compared to placebo.

Echocardiographic Measurements

Next, we measured the impact of GHRH-A and rrGH on cardiac structure and function following MI. Baseline echocardiography documented similar parameters of LV dimension and function in all groups (FIGS. 1A-D, Table S1). As expected, MI led to a time-dependent increase in LV chamber dimensions and a reduction in ejection fraction (EF) and fraction shortening (FS). Treatment with GHRH-A, but not with rrGH, attenuated the MI-induced increase in LV end-systolic dimension (LVESD). In addition, the reduction in EF due to MI was ameliorated by GHRH-A (47±4% vs. 38±3%, p<0.05) but not by rrGH (44±2%, p=NS), both compared to placebo. Similarly, a reduction in FS from 57±1 to 18.5±0.9% (p<0.05) due to MI was improved in the GHRH-A (28.7±3.3%, p<0.05) but not in the rrGH group (20.3±1.3%, p=NS) both compared to placebo.

Hemodynamic Measurements

Figure 1:
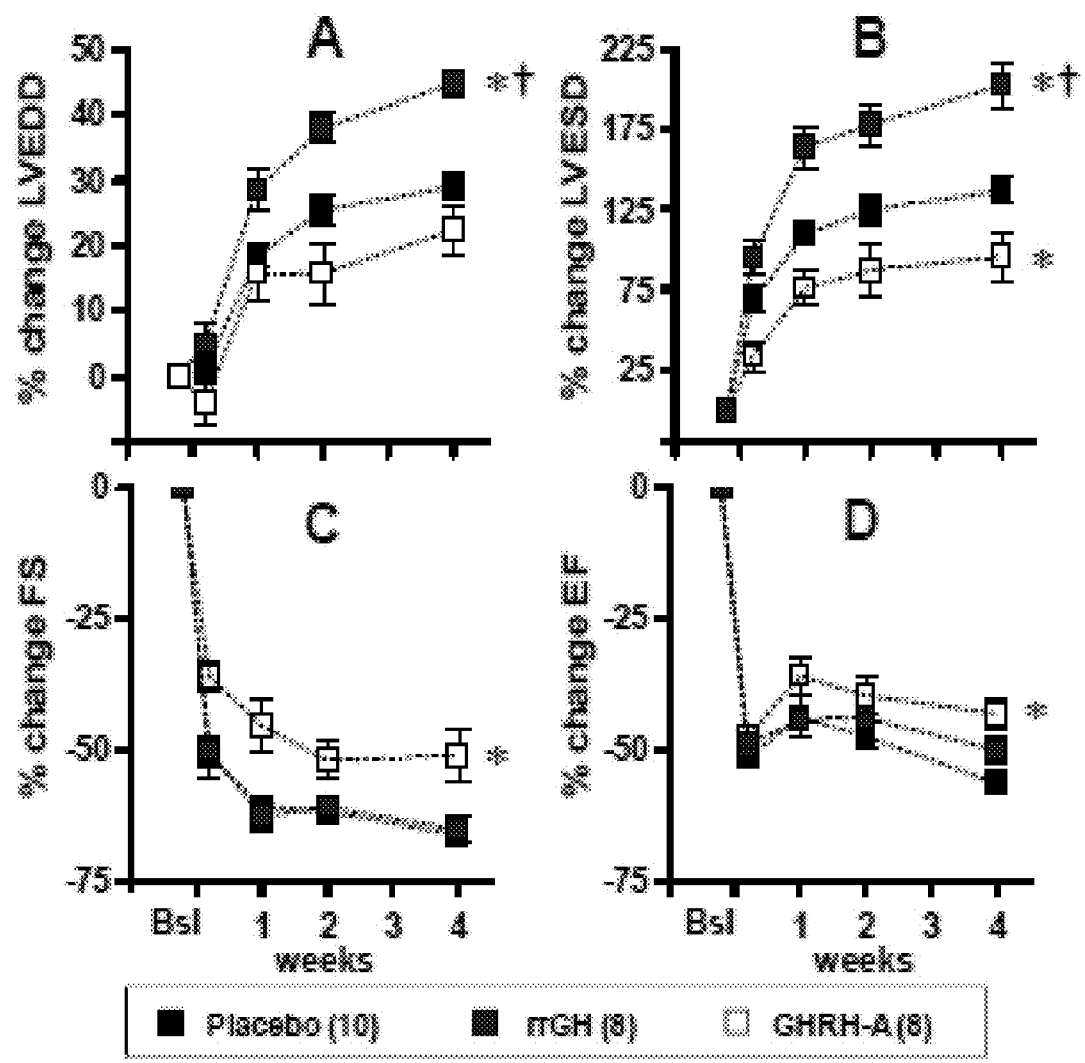
FIG. 1. Changes over time in LV diastolic (A: *$p<0.05$ vs. placebo, † $p<0.01$ vs. GHRH-A) and systolic (B: *$p<0.01$ vs. GHRH-A) dimensions, EF (C: *$p<0.05$ vs. placebo) and FS (D: *$p<0.05$ vs. placebo and GHRH-A).
Figure 2:
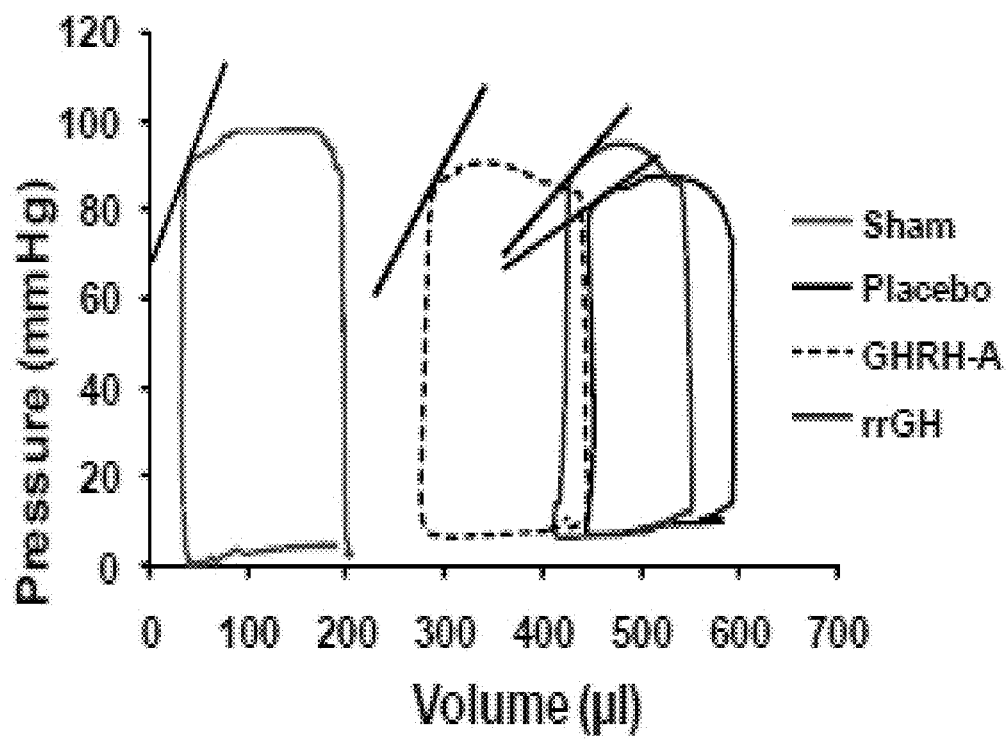
FIG. 2. Representative pressure-volume loops from Sham, MI Placebo, rrGH and GHRH-A groups.

To directly assess the impact of these interventions on cardiac contractile performance and to separate the effects of GHRH-A on cardiac contractility and cardiovascular loading conditions, we performed in vivo hemodynamic analysis (Table 1, FIG. 2). Treatment with GHRH-A but not rrGH caused an increase in both stroke volume (SV) and cardiac output (CO) relative to placebo. This increase in cardiac performance was attributed, at least partially, to a reduction in ventricular afterload, measured as arterial elastance (Ea). Interestingly, Ea was actually increased with rrGH. LV end-systolic (LVESP) and end-diastolic (LVEDP) pressures were similar in all groups. Consistent with the echocardiographic data, EF was higher in GHRH-A than in placebo or rrGH group. Similarly, stroke work (SW) was increased in GHRH-A group vs. placebo or rrGH. With regard to myocardial contractility, the peak rate of pressure rise (dP/dt$_{max}$) was increased in the GHRH-A group in comparison to placebo and rrGH groups, while there were no significant difference in the peak rate of pressure decline (dP/dt$_{min}$) and the relaxation time constant (Tau); however, treatment with GHRH-A trended to increase preload-recruitable stroke work (PRSW) and the relationship between dP/dt$_{max}$ and end-diastolic volume (EDV) (dP/dt$_{max}$_EDV). Conversely, the ratio between arterial elastance (Ea) and end-systolic elastance (Ees) trended to be lower in the GHRH-A group.

Histopathology

Figure 3:
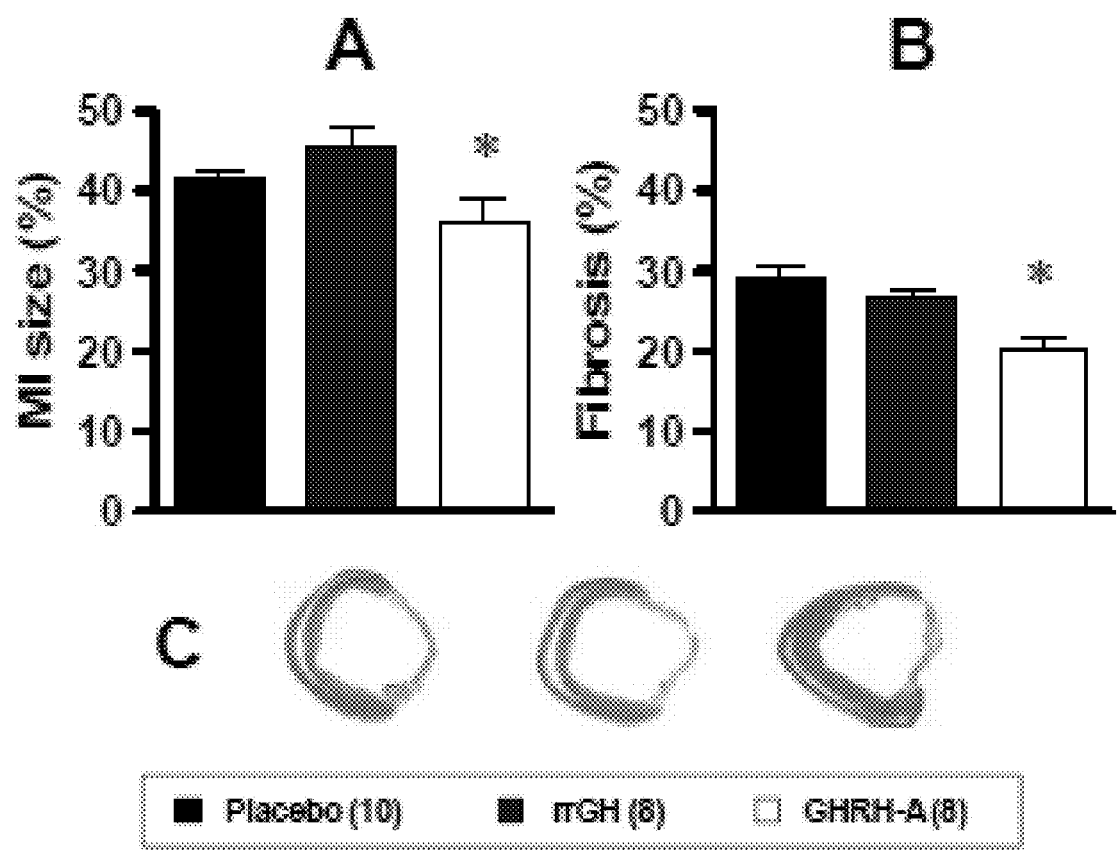
FIG. 3. Bar graphs showing infarct size (A) and percentage of fibrosis (B). Representative Masson's trichrome-stained histological sections (C) for infarct size measurement. The infarct size (MI %) was significantly attenuated in GHRH-A group (*$p=0.011$ vs. placebo and rrGH). Similarly, the percentage of fibrosis was reduced in GHRH-A group (*$p=0.0002$ vs. placebo and rrGH)

MI size (FIG. 3A) in rrGH and placebo groups was similar (45±2 vs. 41±1%, respectively) while GHRH-A rats had reduced MI size (36±3%, p<0.05 vs. placebo and rrGH). The reduced infarct burden was also reflected in the percentage of ventricular fibrosis (FIG. 3B), which was strikingly reduced with GHRH-A (20±1%) in comparison to placebo (29±1%) and rrGH (27±1%)(p<0.01 for both), whereas, capillary density (Fig. S3A) was higher in rrGH (0.02±0.002/mm$^2$) than in placebo or GHRH-A groups (0.01±0.001 and 0.006±0.001/mm$^2$, respectively) (p<0.001 for both). The width of myocytes was not different among groups (Fig. S3B).

GHRH Receptor

Figure 4:
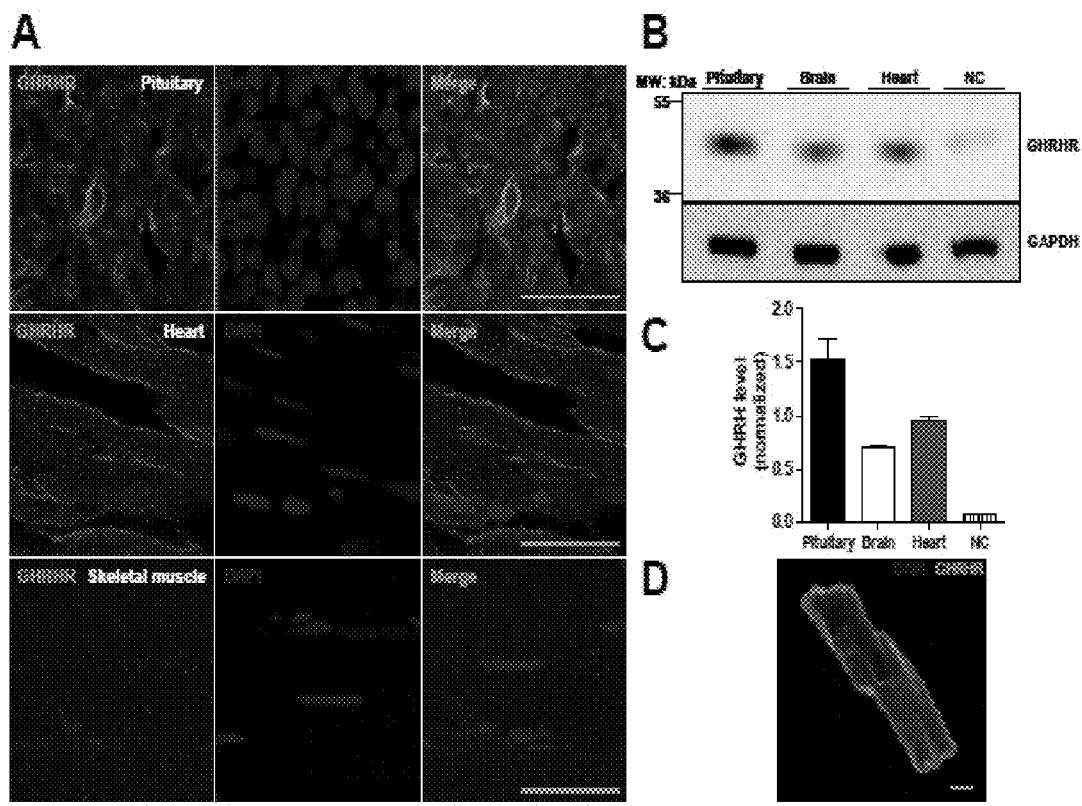
FIG. 4. A: Cryosections (A) of pituitary (top panel), heart (mid panel) and skeletal muscle (bottom panel) incubated with GHRHR (green). Scale bar: 50 μm. GHRHR specificity is demonstrated by intense immunohistochemical reactivity in pituitary (positive control) and heart; negative results are observed in skeletal muscle (negative control). B: Western blotting detected a 47 kDa protein corresponding to GHRHR. Molecular weight markers are indicated on the left side of the panel (NC: negative control). C: GHRHR protein abundance measured by Western blotting analysis and expressed in arbitrary units. D: Representative confocal micrograph image showing the presence of GHRHR (green) on cardiomyocyte sarcolemmal membrane. Scale bar: 10 m.

The presence or absence of GHRH-R was detected in frozen sections of pituitary, heart and, skeletal muscle under fluorescent and confocal microscopy (FIG. 4A) and the intensity of the fluorescence of the GHRHR was measured in paraffin tissues of treated and non-treated rats (Fig. S4). The expression of GHRH-R was confirmed by Western blotting (FIGS. 4B-C) and the GHRH-R was also detected within cardiomyocytes (FIG. 4D). In addition, using real-time polymerase chain reaction (rt-qPCR) we demonstrated the presence of mRNA for GHRH receptor in rat heart (Tables S2-S3, Fig. S5A-B) and the radioligand binding studies revealed that the ischemic rat heart samples showed specific high affinity binding sites for GHRH antagonist, JV-1-42 ligand, characterized by a K$_d$ of 0.86 nM and a B$_{max}$ of 51.28 fmol/mg protein.

Impact on Cellular Division and Proliferation

Figure 5:
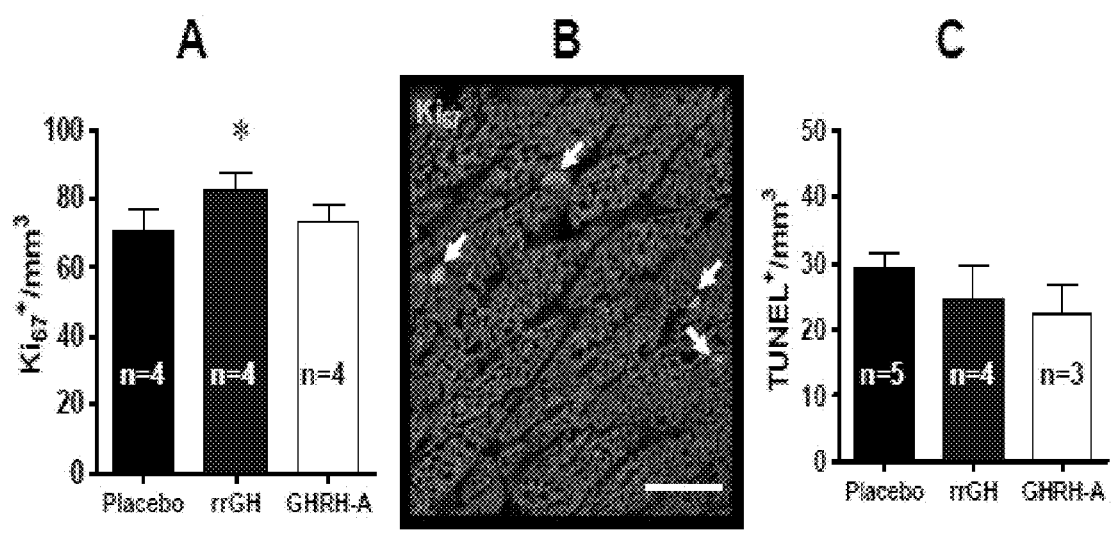
FIG. 5. Bar graphs showing the expression of cells positively stained for $Ki_{67}$ (A) in the remote zone (*$p<0.05$ vs. placebo and GHRH-A). Panel B depicts a representative confocal micrograph image of $Ki_{67}$ positive cells (green, white arrows), tropomyosin (red) and DAPI (blue). Scale bar: 20 m. Panel C: Bar graphs showing the expression of TUNEL positive cells per unit area ($mm^3$).
Figure 6:
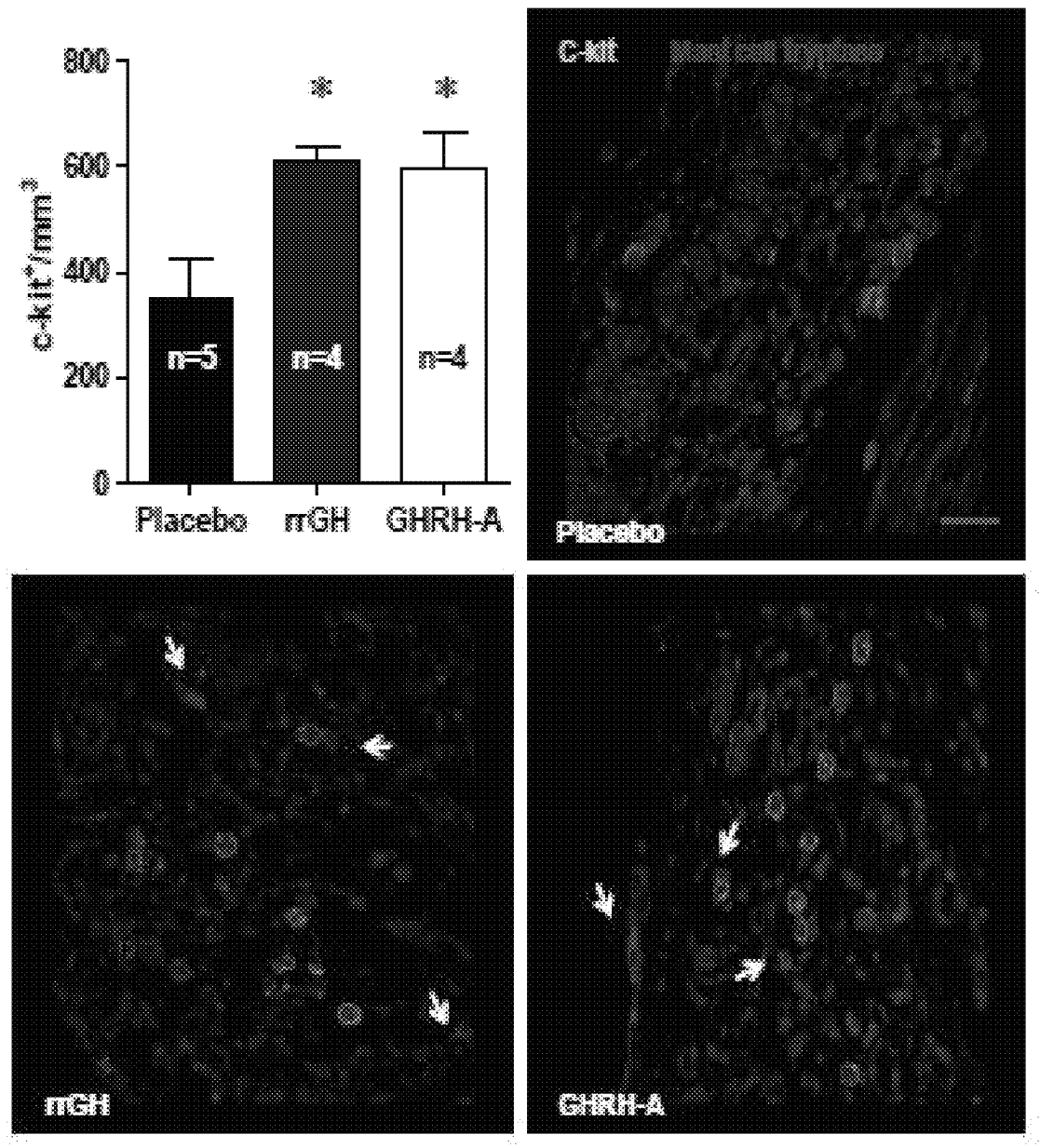
FIG. 6. Representative images of c-kit$^+$ cells in the infarct zone observed under confocal microscopy. Panels depict representative triple staining for mast cell tryptase (red), c-kit (green) and nuclei (blue) obtained from placebo (top right), rrGH (bottom left) and GHRH-A (bottom right). Arrows correspond to examples of mast cell Scale bar: 20 m. Bar graph showing the high expression of c-kit$^+$ cells per unit area ($mm^3$) in rrGH and GHRH-A treated rats. (*$p<0.05$ vs. placebo)
Figure 7:
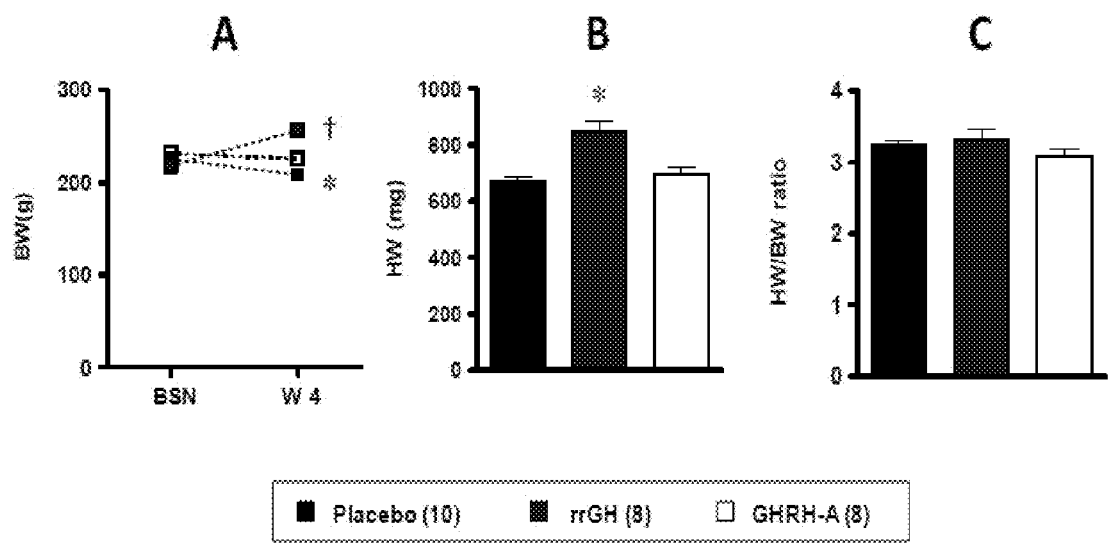
FIG. 7. Changes over time in body weight (BW) after MI (A: *$p<0.05$ vs. baseline; † $p<0.01$ vs. BSN and placebo at week 4). Effects of 4-week treatment with rrGH or GHRH-A on heart weight (HW) and the ratio HW/BW (B and C, respectively; *$p<0.0001$ vs. placebo and GHRH-A). All values represent means±SEM.
Figure 8:
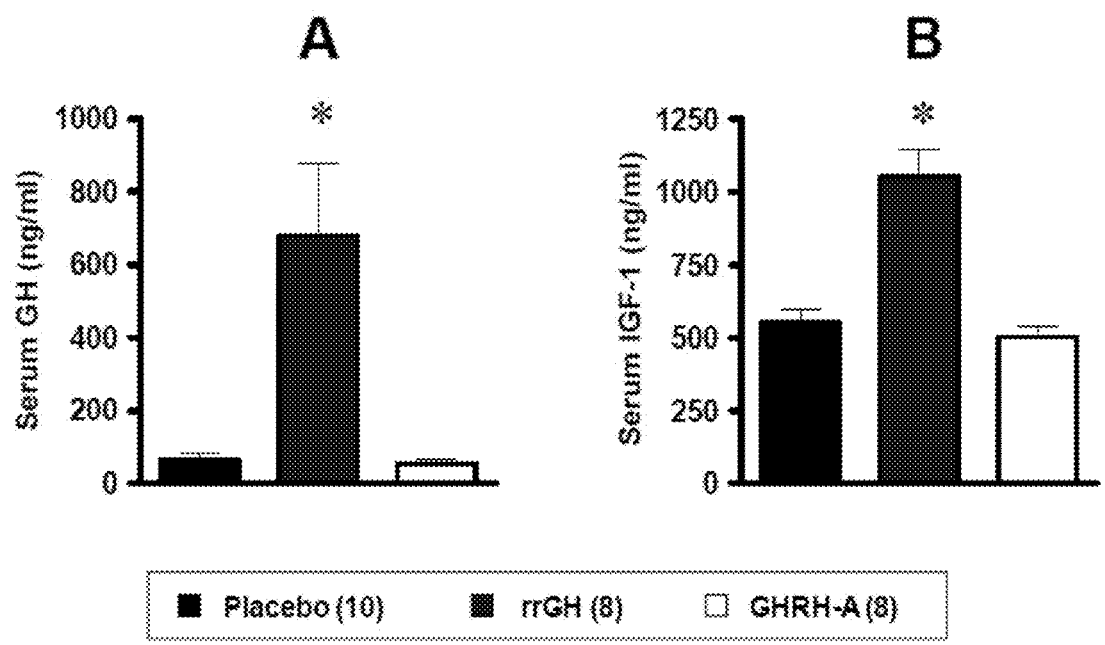
FIG. 8. Serum concentration (ng/ml) of GH (A) and IGF-I (B) measured after 4-week treatment with placebo, rrGH or GHRH-A. All values represent means±SEM. (*$p<0.01$ vs. placebo and GHRH-A)
Figure 9:
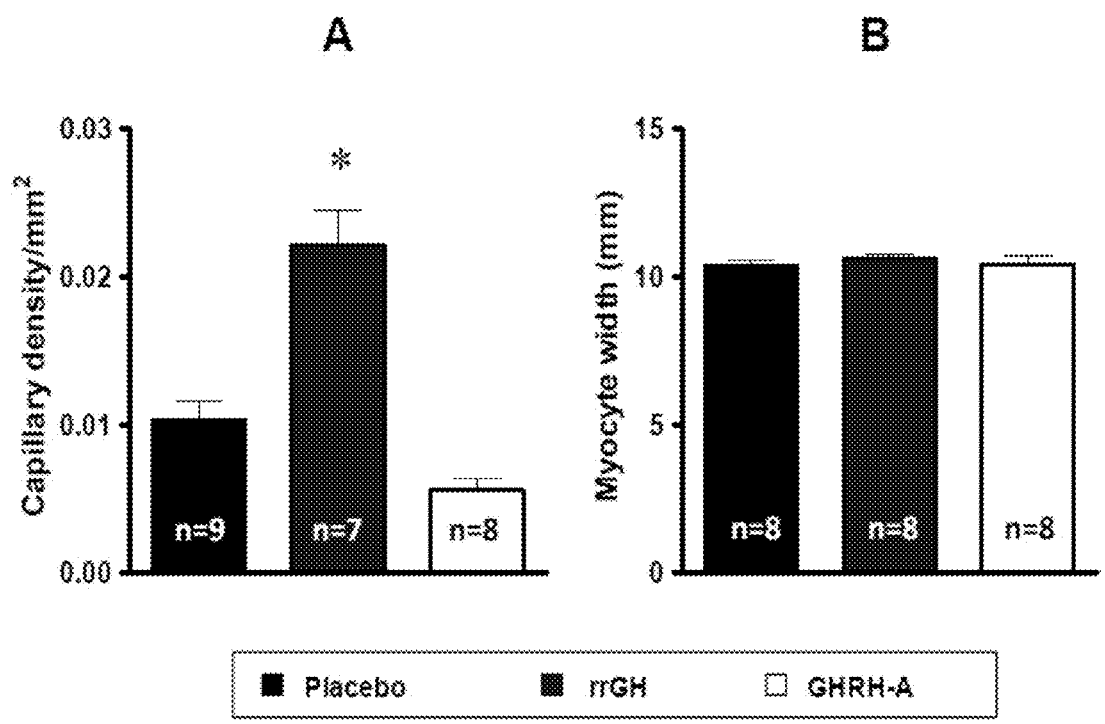
FIG. 9. Bar graphs showing capillary density (A) and myocyte width (B) measurements (*p<0.001 vs. placebo and GHRH-A).
Figure 10:
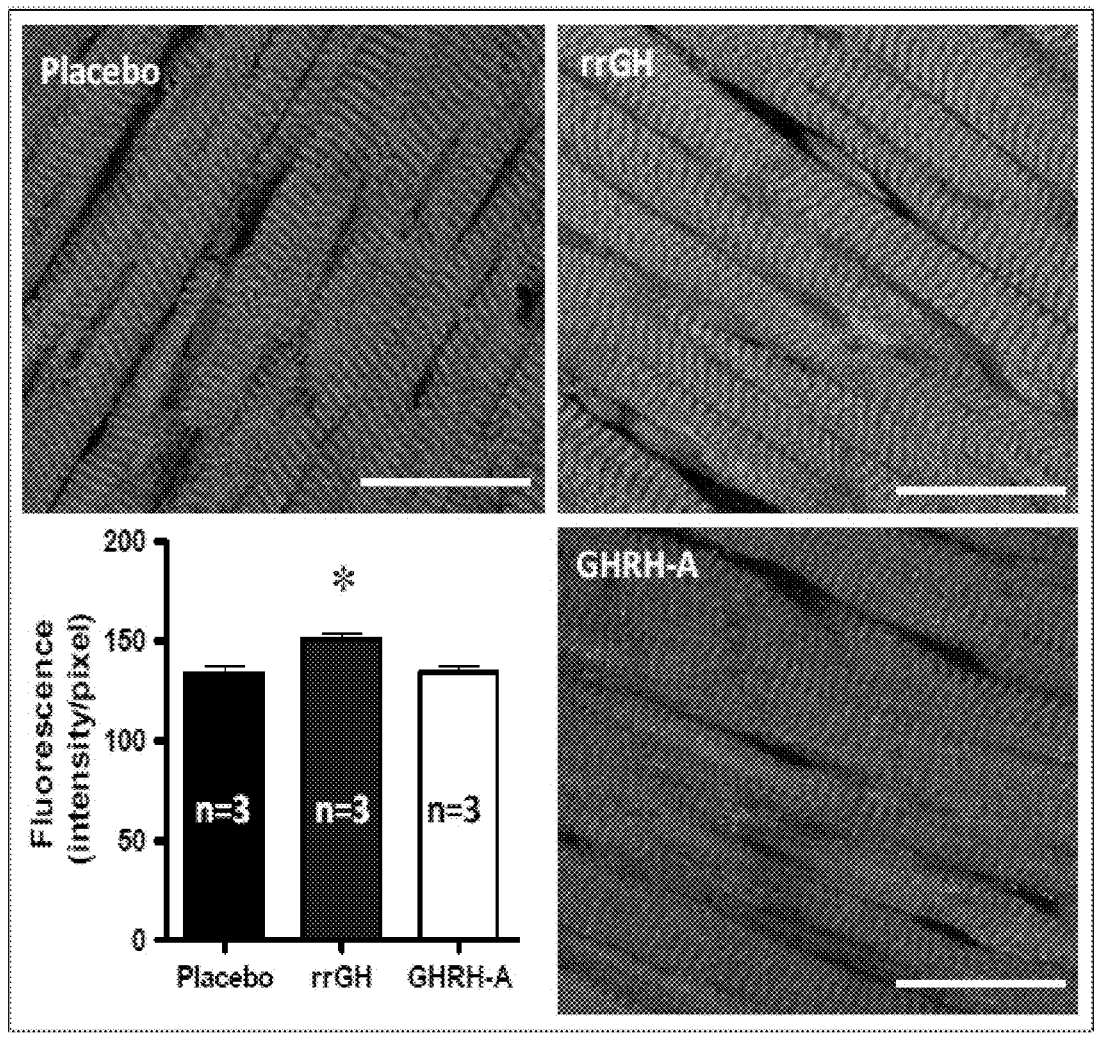
FIG. 10. Representative confocal micrograph of the expression of GHRHR on cardiomyocytes from rats treated with placebo, rrGH or GHRH-A. Scale bar: 50 m. Bar graphs show the intensity of fluoresnicence (intensity/pixel). *p<0.01 vs. placebo and † p<0.0001 vs. GHRH-A.
Figure 11:
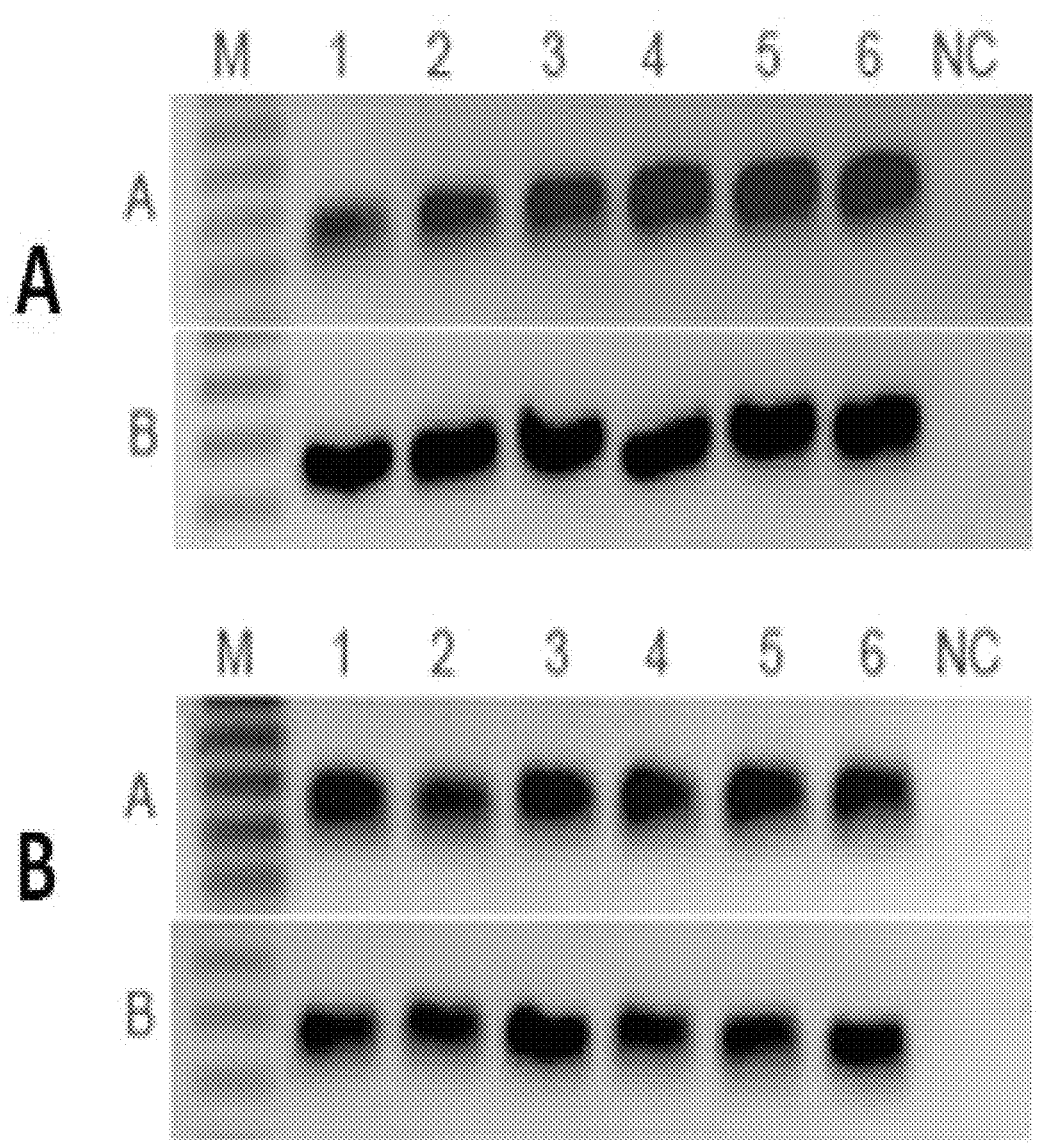
FIG. 11. RT-PCR analysis of GHRH-R (a) and β-actin (b) in representative samples of rat heart tissues. A. Lanes 1, 2, 3 represent placebo samples and lanes 4, 5 and 6 represent rrGH (A) treated samples. B. Lanes 1, 2, 3 represent placebo samples and lanes 4, 5 and 6 represent JI-38 (B) treated samples. DNA molecular weight marker is presented in lane M.

Immunostaining for Ki$_{67}$ positive myocytes and non-myocytes revealed no differences between the border and infarct zones, however, in the remote zone, the expression of Ki$_{67}$ positive cells was higher in the rrGH relative to placebo and GHRH-A groups (p<0.01 for both) (FIGS. 5A-B). Next we measured the proliferation of endogenous c-kit+ cardiac precursor cells. Importantly, the expression of c-kit+ cells (mast cells excluded) per $mm^3$ was higher (p=0.02) in both treated groups than in placebo (FIG. 6).

TUNEL staining (FIG. 5C) did not show differences between groups. On the other hand, rt-qPCR, revealed that the expression of an anti-apoptotic gene (Bcl2) was upregulated in GHRH-A (p=0.07), while the pro-apoptotic gene (Bax) trended to be downregulated in the same group (p=0.207). Accordingly, the ratio between Bax and Bcl2 expression was significantly reduced in the GHRH-A group in comparison to placebo or rrGH treated rats (p=0.03).

TABLE 1

Hemodynamic parameters and indices of systolic and diastolic function derived from pressure-volume relationships.

|  | Placebo (8) | rrGH (6) | GHRH-A (8) |
|---|---|---|---|
| Heart rate (bpm) | 256 ± 6.6 | 247 ± 6.8 | 270 ± 17 |
| Integrated performance |  |  |  |
| EF (%) | 29.8 ± 1.4 | 26.2 ± 1.7 | 36.9 ± 2.6 * † |
| SW (mmHg x l) | 9424 ± 1158 | 6920 ± 790 | 12000 ± 866 * † |
| SV (µl) | 131 ± 20 | 98 ± 13 | 161 ± 12 ‡ |
| CO (ml/min) | 30.5 ± 5.0 | 22.5 ± 3.4 | 40.1 ± 3.1 * † |
| Ea/Ees | 4.1 ± 0.7 | 4.4 ± 0.6 | 3.2 ± 0.3 |
| Afterload |  |  |  |
| LVESP (mmHg) | 85 ± 1.8 | 91 ± 2.3 | 83 ± 1.1 |
| Ea (mmHg/µl) | 0.8 ± 0.1 | 1.1 ± 0.2 | 0.5 ± 0.004 * † |
| Preload |  |  |  |
| LVEDP (mmHg) | 9.8 ± 0.6 | 10 ± 1.8 | 8 ± 0.5 |
| LVEDV (µl) | 413 ± 56 | 351 ± 38 | 421 ± 26 |
| Contractility |  |  |  |
| $dP/dt_{max}$ (mmHg/s) | 6198 ± 194 | 6243 ± 313 | 6986 ± 163 ‡ |
| $dP/dt_{max}$_EDV (mmHg/s/l) | 22.3 ± 8.1 | 17.5 ± 4.3 | 42.5 ± 12.9 |
| Ees (mmHg/l) | 0.26 ± 0.09 | 0.33 ± 0.12 | 0.19 ± 0.02 |
| PRSW (mmHg) | 45 ± 3.6 | 48 ± 5.0 | 53 ± 2.1 |
| Lusitropy |  |  |  |
| dP/dtmin (mmHg/s) | 3986 ± 177 | 4028 ± 334 | 3989 ± 106 |
| TAU (G) (ms) | 16.8 ± 0.9 | 19.9 ± 0.4 | 16.9 ± 0.5 |

Ejection fraction (EF), stroke work (SW), stroke volume (SV), cardiac output (CO), ratio between arterial elastance and end-systolic elastance (Ea/Ees), left ventricular end-systolic pressure (LVESP), arterial elastance (Ea), left ventricular end-diastolic pressure (LVEDP), left ventricular end-diastolic volume (LVEDV), peak rate of the pressure rise ($dP/dt_{max}$), relationship between $dP/dt_{max}$ and end-diastolic volume ($dP/dt_{max}$_EDV), end-systolic elastance (Ees), preload recruitable stroke work (PRSW), peak rate of pressure decline ($dP/dt_{min}$), relaxation time constant calculated by Glantz method (TAU).

Supporting Information Material and Methods
Echocardiographic Measurements

Echocardiographic measurements were obtained at baseline, 2 days, 1, 2 and 4 weeks. Echocardiographic assessments were performed in anesthetized rats (2% isoflurane inhalation) using a Vevo-770 echocardiogram (Visual Sonics Inc., Toronto, Ontario, Canada) equipped with a 17.5-MHz transducer. Cardiac dimensions: LV end diastolic (LVEDD), end systolic (LVESD) diameters and fractional shortening (FS) were recorded from M-mode images using averaged measurements from 3 to 5 consecutive cardiac cycles according to the American Society of Echocardiography (1). Ejection fraction (EF) was calculated from bi-dimensional long-axis parasternal views taken through the infarcted area. All images were analyzed using Vevo 770 3.0.0 software (Visual Sonics Inc., Toronto, Ontario, Canada).

Hemodynamic Measurements

Rats were anesthetized by intramuscular injection of a mixture of ketamine (100 mg/kg), xylazine (20 mg/kg) and acepromazine (10 mg/kg). A 2-F micromanometer tipped catheter (SPR-838, Millar Instruments, Houston, Tex.) was inserted into the right carotid artery and advanced retrograde into the left ventricle. Measurements were calibrated by injecting a hypertonic saline (15%) bolus to determine extra-ventricular conductance; relative volume units were converted to actual volume using the cuvette calibration method (2). All analyses were performed using PVAN 3.0 software (Millar Instruments, Houston, Tex.). Left ventricular pressure-volume relations were assessed by transiently compressing the inferior vena cava.

Tissue Collection

At the end of the study, rat hearts were harvested for further analysis. Hearts were weighted and the basal portion, free of fibrotic tissue, was flash-frozen in liquid nitrogen for total RNA isolation and protein analysis. Remaining tissue was fixed with 10% formalin for histology.

Histology

Slides were prepared with H&E and Masson's trichrome stain to assess cardiac structure and the presence and extent of fibrosis and myocardial scar, respectively. The size of MI was determined using NIH Image version 1.30v for Windows to quantify the percentage area of fibrosis. An image-processing software (Imaging Processing Toolkit 5.0, Reindeer Graphics, Asheville, N.C.) and Adobe Photoshop CS2 (San Jose, Calif.) were used to assess the slides as previously described with minor modifications (3). The percentage of fibrosis was calculated by using the following formula:

% fibrosis=fibrotic area/(fibrotic area+healthy area)

H&E stained sections of hearts from midventricular level were used to measure the myocyte width. At least 35-50 cardiomyocytes were counted and averaged at the level of the nuclei in non-infarcted remote myocardium.

Total RNA Isolation

Total RNA from heart tissue was extracted using Trizol (Invitrogen, Carlsbad, Calif.). The quality of RNA isolated was tested using NanoDrop1000 (Thermo Fisher Scientific Inc., Wilmington, Del.). OD 260/280 ratio was in the range of 1.8 to 2.1 for all samples.

Myocyte Isolation

The isolation of myocytes was performed as previously described (4). Briefly; the rats were anesthetized with pentobarbital (100 mg/Kg, Sigma, St. Louis, Mo.) with heparin (4000 U/Kg, APP Pharmaceuticals, Schaumburg, Ill.). For the isolation of myocytes, the hearts were cannulated and perfused through the aorta with $Ca^{2+}$ free bicarbonate buffer containing 120 mM NaCl, 5.4 KCl, 1.2 mM $MgSO_4$, 1.2 mM $NaH_2PO_4$, 20 mM $NaHCO_3$, 10 mM 2,3-butanedione monoxime, 5 mM taurine and, 5.6 mM glucose, gassed with 95% O2-5% CO2. This was followed by enzymatic digestion with collagenase type-2 (1 mg/ml, Worthington Biochemical Co., Lakewood, N.J.) and protease type-XIV (0.1 mg/ml, Sigma, St. Louis, Mo.).

Cardiomyocytes were obtained from digested hearts followed by mechanical disruption, by filtration, centrifugation, and resuspension in a Tyrode solution containing 0.125 mM $CaCl_2$, 144 mM NaCl, 1 mM $MgCl_2$, 10 mM HEPES, 5.6 mM glucose, 1.2 mM $NaHPO_4$, 5 mM KCl, pH7.4.

GH and IGF-I Measurements

At the end of the study, blood was drawn 1-2 hours after the last rrGH or GHRH-A injection and the serum was stored at −80° C. until the measurements were done. All the samples were assayed together and each sample was assayed in duplicate. Rat serum GH was measured using a rat GH Enzyme-Linked Immunosorbent Assay (ELISA) Kit (DSL-10-72100, DSL Webster, Tex.), following the manufacturer's recommendations. This test is an enzymatically amplified "one-step" sandwich-type enzyme immunoassay, where standards, controls and unknown samples are incubated in microtitration wells precoated with the anti-rat GH antibody. The standard curve of the assay was established with samples provided by the manufacturer. Rat serum IGF-I was measured using a rat IGF-I Radioimmunoassay Kit (DSL-2900, DSL Webster, Tex.), after extraction with acid ethanol, following the manufacturer's recommendations. The IGF-I assay included quality controls provided by the manufacturer. The standard curve of the assay was established with samples provided by the manufacturer.

GHRH Receptors

The expression of GHRHR was measured by immunofluorescence and real time PCR. The detection of GHRHR protein was carried out by Western blotting using the method of Schulz et al (5). The binding affinity of GHRHR was demonstrated by radioligand binding assay (see details in each section, respectively).

Immunostaining

Cardiomyocytes were stained as described. Briefly, after isolation, 150 µl of cardiomyocytes in suspension were allowed to sediment and then fixed for 10 minutes (2% paraformaldehyde). Cells were stained with rabbit polyclonal antibody against human GHRH-R at 4° C. for 24 hours followed by the secondary antibody at 37° C. for 1 hour (see table with a list of antibodies in Supplemental Information). Frozen sections were used for positive controls (pituitary) and negative controls (skeletal muscle).

Paraffin sections were deparaffinized and rehydrated by immersion in xylene and a graded series of ethanols. Antigen retrieval was performed by a heat-induced method with citrate buffer (Dako, Carpinteria, Calif.). After blocking with 10% normal donkey serum, sections were incubated with a primary antibody (table S3), at 37° C. for 1 hour, followed by application of secondary antibody. Omission of the primary antibodies on parallel sections was used as negative control. Nuclei were counterstained with DAPI (Invitrogen, Carlsbad, Calif.). The total numbers of positively-stained cells were quantified per slide to calculate the number of cells per unit volume ($mm^3$) on each sample. Morphometric analysis was performed by using Adobe Photoshop CS3 (San Jose, Calif.)

To quantify apoptosis of cardiac cells, terminal deoxynucleotidyl transferase-mediated dUTP nick end-labeling (TUNEL) staining was performed on paraffin embedded tissue sections according to the manufacturer's protocol using a commercially available kit (In Situ Cell Death Detection Kit, POD, Roche Diagnostics GmbH, Germany). Slides were analyzed by fluorescent microscopy under 40× magnifications. Apoptotic nuclei were identified by green fluorescence staining and expressed as a percentage per millimeter cubic ($mm^3$) from tissue sections per animal. All images were obtained with both fluorescent (Olympus IX81, Olympus America Inc., Center Valley, Pa.) and a LSM710 Zeiss confocal laser scanning module (Carl Zeiss MicroImaging GmbH, Germany).

Quantification of Immunohistochemistry Staining for GHRHR

All images were obtained using a 40× objective and the settings were kept the same for the entire study. Ten high power fields of confocal images were taken from each sample (n=3 for each group) (Figure S4). The quantification of the fluorescence intensity was performed following deconvolution, using Huygen Essential software, version 3.4 (Scientific Volume Imaging, Hilversum, The Netherlands). An optical density plot of the selected area was generated using the histogram tool in the Image Pro plus version 6.3 (Media Cybernetics, MD) and the mean staining intensity (intensity/pixel) was recorded.

Real Time PCR

The expression of GHRHR was measured using real-time quantitative PCR as described previously by Havt et al (6).

We evaluated the mRNA expression of rat GHRH receptor (GHRH-R) and β-actin. The probes designed to evaluate the expression of GHRH-R and β-actin are 5'-/Cy5/ACC TCC GAC TTT CTC AGT TCC TGT ATG CCC/BHQ_2/-3' and 5'-/6-FAM/ATC CTG CGT CTG GAC CTG GCT GGC/BHQ_1/-3', respectively. Gene specific primer sequences were the following: GHRH-R (sense) 5'-TCTGCTTTCTCTAGGTCCCTGT-3' and 5'-TGGTTTCCCTGGGCCTTGG-3' (antisense) with a product size of 110 bp, β-actin: (sense) 5'-GGGTTACGCGCTCCCTCAT-3' and 5'-GTCACGCACGATTTCCCTCTC-3' (antisense) with a product size of 133 bp.

All real-time PCR reactions were performed in the iCycler iQ™ Real-Time PCR Detection System (Bio-Rad, Hercules, Calif.). Thermal cycling conditions comprised an initial denaturation step at 95° C. for 3 min followed by 45 cycles at 95° C. for 30 sec and an annealing temperature at 60° C. for GHRH-R and β-actin for 1 min. As final steps, we included two cycles: one at 95° C. and the other at 60° C., both for 1 min. All samples were run in triplicate and each well of PCR reactions contained 25 µL as final volume including 2 µL of cDNA, 200 nM of gene specific primers and 400 nM of probes. iQ™ Supermix (Bio-Rad) was used in the PCR. The efficiencies of all primers (Invitrogen Life Technologies, Carlsbad, Calif.) and probes (Integrated DNA Technologies, Coralville, Iowa) were tested prior to the experiments and they were all efficient in the range of 95-105%. Normal rat pituitary was used as positive control and rat β-actin as housekeeping gene. Negative samples were run in each reaction consisting of no-RNA in reverse transcriptase reaction and no-cDNA in PCR reaction. Two microliters of each amplification reaction was electrophoretically separated on 1.5% agarose gel, stained with SYBR® Green I (Lonza, Rockland, Me.), and visualized under UV light.

The mathematical method described by Pfaffl (7) was used to evaluate the relative expression ratio for GHRH-R compared with β-actin, with the efficiencies for each set of real-time PCR reactions and the threshold cycle ($C_T$).

The monitoring of pro-apoptotic and anti-apoptotic genes was also assessed by real time PCR. First-strand cDNA was synthesized from 1 µg total RNA using the High-Capacity cDNA Reverse-Transcription Kit (Applied Biosystems, Inc., Foster City, Calif., USA), and ribosomal 18S RNA served as the housekeeping gene. We used TaqMan probes labeled with 6-carboxyfluorescein (FAM) for real-time RT-PCR reactions, according to manufacturer's protocol (Applied Biosystems, Inc., Foster City, Calif., USA). Data were analyzed by the threshold cycle (Ct) relative quantification method.

Western Blotting

The detection of GHRHR protein Immunoblot analysis was performed as described. Equal amount of proteins (80 µg) from rat pituitary, brain, heart and liver for negative control were resolved in 12% SDS-PAGE and incubated overnight with rabbit polyclonal anti-human GHRHR antibody (Abcam, 1/1000) at 4° C.

Radioligand Binding Studies

Radioiodinated derivatives of GHRH antagonist JV-1-42 were prepared by the chloramine-T method as described by Halmos et al (8, 9). Preparation of membrane fractions from ischemic rat heart samples was performed as reported by Halmos et al (8). Binding characteristics of GHRH binding sites were determined by in vitro ligand competition assays based on the binding of radiolabeled JV-1-42 to heart membrane fractions. Binding affinity ($K_d$) and capacity ($B_{max}$) were calculated by the Prism 4.0.1 (GraphPad Software, Inc., La Jolla, Calif.).

Statistical Analysis

All values are shown as mean±SEM. Echocardiographic parameters during a 4-week follow-up were compared within and between groups using one-way ANOVA for repeated measurements and two-way ANOVA followed by post-hoc tests, respectively. For a given parameter, $p < 0.05$ was considered significant. All tests were carried out using Sigma Stat 3.5 (Jandel, San Rafael, Calif.).

TABLE 2

Echocardiographic measurements at baseline (BSL) and at 4 weeks (W4) post-MI.

|  |  | PLACEBO (10) | rrGH (8) | GHRH-A (8) |
|---|---|---|---|---|
| LVEDD (mm) | BSL | 6.1 ± 0.1 | 5.9 ± 0.1 | 6.3 ± 0.2 |
|  | W4 | 7.9 ± 0.1 | 8.6 ± 0.1 * | 7.7 ± 0.2 |
| LVESD (mm) | BSL | 2.7 ± 0.1 | 2.3 ± 0.1 | 2.9 ± 0.1 |
|  | W4 | 6.4 ± 0.1 | 6.8 ± 0.2 † | 5.7 ± 0.3 ‡ |
| FS (%) | BSL | 55.5 ± 1.2 | 58.2 ± 0.7 | 53.1 ± 1.0 |
|  | W4 | 18.5 ± 0.9 | 20.3 ± 1.3 | 28.7 ± 3.3 § |
| EF (%) | BSL | 84.5 ± 1.4 | 89.2 ± 0.4 | 85.7 ± 1.6 |
|  | W4 | 38.3 ± 3.4 | 44.3 ± 2.3 | 47.2 ± 4.0 ¶ |

Left ventricle end-diastolic diameter (LVEDD), left ventricle end-systolic diameter (LVESD), fraction shortening (FS) and ejection fraction (EF).

TABLE 3

Real-Time PCR values of the relative expression of mRNA for GHRH-R and β-actin in rat heart tissue samples after treatment with rrGH.

|  | Placebo Ct values, mean_SEM, | rrGH Ct values, mean_SEM | Ratio |
|---|---|---|---|
| GHRH-R | 28.74 ± 0.12 | 27.81 ± 0.05 | 2.10 * |
| β-actin | 17.87 ± 0.11 | 17.84 ± 0.12 | — |

The ratio represents the gene expression level in the treatment group as compared to the placebo group (*$p < 0.05$ versus placebo).

TABLE 4

Real-time PCR values of the relative expression of mRNA for GHRH-R and β-actin in rat heart tissue samples after treatment with GHRH-A (JI-38).

|  | Placebo Ct values, mean_SEM | JI-38 Ct values, mean_SEM | Ratio |
|---|---|---|---|
| GHRH-R | 32.38 ± 0.42 | 32.96 ± 0.18 | 1.91 |
| β-actin | 20.72 ± 0.61 | 22.33 ± 0.03 | — |

The ratio represents the gene expression level in the treatment group as compared to the placebo group.

TABLE 5

Antibody list

| Protein | Antibody | Labeling | Fluorochromes |
|---|---|---|---|
| GHRHR | rabbit polyclonal | indirect | F |
| c-kit | goat polyclonal | indirect | F |
| Mast cell tryptase | mouse polyclonal | indirect | T |
| Ki67 | rabbit polyclonal | indirect | F |
| Tropomyosin | mouse polyclonal | indirect | T |
| Nuclear DNA | DAPI | N/A |  |
| TUNEL | Tdt/dUTP | direct | F |

Direct labeling: primary antibody conjugated with the fluorochrome
Indirect labeling: species-specific secondary antibody with the fluorochrome.
F: fluorescein isothiocyanate, T: tetramethyl rhodamine isothiocyanate, Cy5: cyanine 5

REFERENCES

1. Fazio S et al. (2000) The role of the GH-IGF-I axis in the regulation of myocardial growth: from experimental models to human evidence. *Eur J Endocrinol* 142: 211-216.
2. Cittadini A et al. (2001) Importance of an intact growth hormone/insulin-like growth factor 1 axis for normal post-infarction healing: studies in dwarf rats. *Endocrinology* 142: 332-338.
3. Fazio S et al. (1996) A preliminary study of growth hormone in the treatment of dilated cardiomyopathy. *N Engl J Med* 334: 809-814.
4. Osterziel K J et al. (1998) Randomised, double-blind, placebo-controlled trial of human recombinant growth hormone in patients with chronic heart failure due to dilated cardiomyopathy. *Lancet* 351: 1233-1237.
5. Cittadini A et al. (1997) Growth hormone attenuates early left ventricular remodeling and improves cardiac function in rats with large myocardial infarction. *J Am Coll Cardiol* 29: 1109-1116.
6. Tivesten A et al. (2000) The growth hormone secretagogue hexarelin improves cardiac function in rats after experimental myocardial infarction. *Endocrinology* 141: 60-66.
7. Broglio F et al. (2002) Ghrelin: much more than a natural growth hormone secretagogue. *Isr Med Assoc J* 4: 607-613.
8. Marleau S, Mulumba M, Lamontagne D, Ong H (2006) Cardiac and peripheral actions of growth hormone and its releasing peptides: relevance for the treatment of cardiomyopathies. *Cardiovasc Res* 69: 26-35.
9. Matsubara S et al. (1995) Differential gene expression of growth hormone (GH)-releasing hormone (GRH) and GRH receptor in various rat tissues. *Endocrinology* 136: 4147-4150.
10. Granata R et al. (2009) Growth hormone-releasing hormone promotes survival of cardiac myocytes in vitro and protects against ischaemia-reperfusion injury in rat heart. *Cardiovasc Res* 83: 303-312.
11. Aimaretti G et al. (2004) GHRH and GH secretagogues: clinical perspectives and safety. *Pediatr Endocrinol Rev* 2 Suppl 1: 86-92.
12. Kiaris H, Schally A V, Kalofoutis A (2005) Extrapituitary effects of the growth hormone-releasing hormone. *Vitam Norm* 70:1-24.
13. Izdebski J et al. (1995) Synthesis and biological evaluation of superactive agonists of growth hormone-releasing hormone. *Proc Natl Acad Sci USA* 92: 4872-4876.
14. Cittadini A et al. (2003) Growth hormone prolongs survival in experimental postinfarction heart failure. *J Am Coll Cardiol* 41: 2154-2163.
15. Pagel I et al. (2002) Cardiac and renal effects of growth hormone in volume overload-induced heart failure: role of NO. *Hypertension* 39: 57-62.
16. Bollano E et al. (2001) Growth hormone alone or combined with metoprolol preserves cardiac function after myocardial infarction in rats. *Eur J Heart Fail* 3: 651-660.
17. Omerovic E et al. (2000) Growth hormone improves bioenergetics and decreases catecholamines in postinfarct rat hearts. *Endocrinology* 141: 4592-4599.
18. Mill J G et al. (2005) [The early administration of growth hormone results in deleterious effects on ventricular remodeling after acute myocardial infarction]. *Arq Bras Cardiol* 84: 115-121.
19. Shen Y T et al. (1996) GH replacement fails to improve ventricular function in hypophysectomized rats with myocardial infarction. *Am J Physiol* 271: H1721-H1727.
20. Tivesten A et al. (2001) Similar cardiovascular effects of growth hormone and insulin-like growth factor-I in rats after experimental myocardial infarction. *Growth Horm IGF Res* 11: 187-195.
21. Isgaard J et al. (1997) Growth hormone improves cardiac function in rats with experimental myocardial infarction. *Eur J Clin Invest* 27: 517-525.
22. Duerr R L et al. (1996) Cardiovascular effects of insulin-like growth factor-1 and growth hormone in chronic left ventricular failure in the rat. *Circulation* 93: 2188-2196.
23. Jorgensen K D et al. (1988) Biosynthetic human growth hormone: subchronic toxicity studies in rats and monkeys. *Pharmacol Toxicol* 62: 329-333.
24. Nagaya N et al. (2001) Chronic administration of ghrelin improves left ventricular dysfunction and attenuates development of cardiac cachexia in rats with heart failure. *Circulation* 104: 1430-1435.
25. Frascarelli S, Ghelardoni S, Ronca-Testoni S, Zucchi R (2003) Effect of ghrelin and synthetic growth hormone secretagogues in normal and ischemic rat heart. *Basic Res Cardiol* 98: 401-405.
26. Mayo K E (1992) Molecular cloning and expression of a pituitary-specific receptor for growth hormone-releasing hormone. *Mol Endocrinol* 6: 1734-1744.
27. Pombo C M, Zalvide J, Gaylinn B D, Dieguez C (2000) Growth hormone-releasing hormone stimulates mitogen-activated protein kinase. *Endocrinology* 141: 2113-2119.
28. Baldanzi G et al. (2002) Ghrelin and des-acyl ghrelin inhibit cell death in cardiomyocytes and endothelial cells through ERK1/2 and PI 3-kinase/AKT. *J Cell Biol* 159: 1029-1037.
29. Lorenz K, Schmitt J P, Vidal M, Lohse M J (2009) Cardiac hypertrophy: targeting Raf/MEK/ERK1/2-signaling. *Int J Biochem Cell Biol* 41: 2351-2355.
30. Brywe K G et al. (2005) Growth hormone-releasing peptide hexarelin reduces neonatal brain injury and alters Akt/glycogen synthase kinase-3beta phosphorylation. *Endocrinology* 146: 4665-4672.
31. Shioi T et al. (2000) The conserved phosphoinositide 3-kinase pathway determines heart size in mice. *EMBO J.* 19: 2537-2548.
32. Shiojima I, Walsh K (2006) Regulation of cardiac growth and coronary angiogenesis by the Akt/PKB signaling pathway. *Genes Dev* 20: 3347-3365.
33. Anversa P, Kajstura J (1998) Ventricular myocytes are not terminally differentiated in the adult mammalian heart. *Circ Res* 83: 1-14.
34. Bersell K, Arab S, Haring B, Kuhn B (2009) Neuregulin1/ErbB4 signaling induces cardiomyocyte proliferation and repair of heart injury. *Cell* 138: 257-270.
35. Bergmann O et al. (2009) Evidence for cardiomyocyte renewal in humans. *Science* 324: 98-102.
36. Bruel A, Christoffersen T E, Nyengaard J R (2007) Growth hormone increases the proliferation of existing cardiac myocytes and the total number of cardiac myocytes in the rat heart. *Cardiovasc Res* 76: 400-408.
37. Fazel S et al. (2006) Cardioprotective c-kit+ cells are from the bone marrow and regulate the myocardial balance of angiogenic cytokines. *J Clin Invest* 116: 1865-1877.
38. Padin-Iruegas M E et al. (2009) Cardiac progenitor cells and biotinylated insulin-like growth factor-1 nanofibers improve endogenous and exogenous myocardial regeneration after infarction. *Circulation* 120: 876-887.
39. Gonzalez A et al. (2008) Activation of cardiac progenitor cells reverses the failing heart senescent phenotype and prolongs lifespan. *Circ Res* 102: 597-606.
40. Kanashiro-Takeuchi R. M et al. (2009) Sex-specific impact of aldosterone receptor antagonism on ventricular remodeling and gene expression after myocardial infarction. *Clinical and Translational Science* 2: 134-142.
41. Sahn D J, DeMaria A, Kisslo J, Weyman A (1978) Recommendations regarding quantitation in M-mode echocardiography: results of a survey of echocardiographic measurements. *Circulation* 58: 1072-1083.
42. Pacher P et al. (2008) Measurement of cardiac function using pressure-volume conductance catheter technique in mice and rats. *Nat Protoc* 3: 1422-1434.
43. Gaspard G J, Pasumarthi K B (2008) Quantification of cardiac fibrosis by colour-subtractive computer-assisted image analysis. *Clin Exp Pharmacol Physiol* 35: 679-686.
44. Gonzalez D R, Beigi F, Treuer A V, Hare J M (2007) Deficient ryanodine receptor S-nitrosylation increases sarcoplasmic reticulum calcium leak and arrhythmogenesis in cardiomyocytes. *Proc Natl Acad Sci USA* 104: 20612-20617.
45. Schulz S, Rocken C, Schulz S (2006) Immunocytochemical localisation of plasma membrane GHRH receptors in human tumours using a novel anti-peptide antibody. *Eur J Cancer* 42: 2390-2396.
46. Havt A et al. (2005) The expression of the pituitary growth hormone-releasing hormone receptor and its splice variants in normal and neoplastic human tissues. *Proc Natl Acad Sci USA* 102: 17424-17429.
47. Pfaffl M W (2001) A new mathematical model for relative Quantification in real-time RT-PCR. *Nucleic Acids Res* 29: e45.
48. Halmos G et al. (2002) Expression of growth hormone-releasing hormone and its receptor splice variants in human prostate cancer. *J Clin Endocrinol Metab* 87: 4707-4714.
49. Halmos G, Rekasi Z, Szoke B, Schally A V (1993) Use of radioreceptor assay and cell superfusion system for in vitro screening of analogs of growth hormone-releasing hormone. *Receptor* 3: 87-97.

We claim:

1. A method of initiating cardiac repair in a patient subsequent to myocardial infarction by administration of a sufficient amount of a synthetic peptide that is GHRH or GHRH-A to activate the growth-hormone-releasing-hormone pathway of said patient.

2. The method of claim 1 wherein the targets of the GHRH or GHRH-A are the cardiac myocytes of said patient.

* * * * *